United States Patent
Gardner et al.

(10) Patent No.: US 10,737,031 B2
(45) Date of Patent: Aug. 11, 2020

(54) MEDICANT INJECTION DEVICE

(71) Applicant: Medline Industries, Inc., Northfield, IL (US)

(72) Inventors: Christopher E. Gardner, Manalapan, NJ (US); Robert Banik, Edgewater, NJ (US); Thomas Leo McGurk, Berwyn, PA (US)

(73) Assignee: Medline Industries, Inc., Northfield, IL (US)

( * ) Notice: Subject to any disclaimer, the term of this patent is extended or adjusted under 35 U.S.C. 154(b) by 365 days.

(21) Appl. No.: 15/653,899

(22) Filed: Jul. 19, 2017

(65) Prior Publication Data
US 2018/0126077 A1    May 10, 2018

Related U.S. Application Data

(62) Division of application No. 14/547,125, filed on Nov. 18, 2014, now Pat. No. 9,737,664.
(Continued)

(51) Int. Cl.
*A61M 5/28* (2006.01)
*A61M 5/24* (2006.01)
(Continued)

(52) U.S. Cl.
CPC ............ *A61M 5/282* (2013.01); *A61M 5/001* (2013.01); *A61M 5/2425* (2013.01); *A61M 5/31* (2013.01);
(Continued)

(58) Field of Classification Search
CPC ............ A61M 2005/312; A61M 5/282; A61M 5/347; A61M 3/0262; A61M 2205/273;
(Continued)

(56) References Cited

U.S. PATENT DOCUMENTS 4,187,845 A * 2/1980 Dror ................. A61M 16/0057
128/205.13
4,870,962 A * 10/1989 Sitnik ............... A61M 16/0075
128/205.13
(Continued)

FOREIGN PATENT DOCUMENTS

WO    8300882     3/1983
WO    8605989    10/1986
(Continued)

OTHER PUBLICATIONS

International Search Report of the International Searching Authority dated Apr. 9, 2015, issued in connection with International Patent Application No. PCT/US14/66244 (5 pages).
(Continued)

*Primary Examiner* — Deanna K Hall
(74) *Attorney, Agent, or Firm* — Fitch, Even, Tabin & Flannery LLP (57) ABSTRACT

A medicant injection device includes a compressible body, a tip, and an outer luer body. The compressible body has a proximal end, a distal end, and a plurality of bellows, and defines an inner cavity for holding a liquid medicant. The tip is positioned at the proximal end of the compressible body. The outer luer body includes internal threads, and is positioned over and engaged with the tip to form a first fitting therewith. The first fitting is configured to be connected with a second fitting. A medicant injection device includes a compressible body having first and second arms, a receptacle interconnected with the compressible body and defining an inner cavity, and a first fitting configured to engage a second fitting. The compressible body is configured to be compressed by forcing the distal end of the first and second arm toward each other.

22 Claims, 10 Drawing Sheets

Related U.S. Application Data (60) Provisional application No. 61/905,621, filed on Nov. 18, 2013.

(51) Int. Cl.
*A61M 5/00* (2006.01)
*A61M 5/34* (2006.01)
*A61M 5/31* (2006.01)

(52) U.S. Cl.
CPC .......... *A61M 5/3134* (2013.01); *A61M 5/347* (2013.01); *A61M 2005/312* (2013.01); *A61M 2005/3142* (2013.01)

(58) Field of Classification Search
CPC ... A61M 5/281; A61M 5/2425; A61M 5/2422
USPC ................................. 604/204, 212, 214, 216
See application file for complete search history.

(56) References Cited

U.S. PATENT DOCUMENTS

| | | |
|---|---|---|
| 6,190,364 B1 | 2/2001 | Imbert |
| 6,315,761 B1 | 11/2001 | Shcherbina |
| 6,332,876 B1 | 12/2001 | Poynter |
| 8,372,045 B2 | 2/2013 | Needle |
| 8,545,479 B2 | 10/2013 | Kitani |
| 9,737,664 B2 | 8/2017 | Gardner |
| 2003/0060749 A1 | 3/2003 | Aneas |
| 2010/0056995 A1 | 3/2010 | Kriesel |
| 2012/0191067 A1 | 7/2012 | Chia |
| 2013/0281940 A1 | 10/2013 | Gelblum |
| 2015/0112263 A1* | 4/2015 | Tremblay .............. B05B 11/048 604/140 |

FOREIGN PATENT DOCUMENTS

| | | |
|---|---|---|
| WO | 2010004206 | 1/2010 |
| WO | 2013158425 | 10/2013 |

OTHER PUBLICATIONS

Written Opinion of the International Searching Authority dated Apr. 9, 2015, issued in connection with International Appln. No. PCT/US14/66244 (7 pages).

Extended European Search Report for European Patent Application No. 14862713.6 dated May 11, 2017; 8 pages.

* cited by examiner

MEDICANT INJECTION DEVICE

RELATED APPLICATIONS

The present application is a division of U.S. patent application Ser. No. 14/547,125 filed on Nov. 18, 2014, which claims the benefit of U.S. Provisional Application No. 61/905,621 filed on Nov. 18, 2013, which is incorporated herein by reference it its entireties.

BACKGROUND

Field

The present invention relates to a medicant injection device and more specifically to a medicant injection device including a compressible container that includes luer features.

Related Art

Prefilled syringes are a common type of injection device utilized in the medical field, and are often utilized for depositing a medicant dosage into a patient. In this regard, prefilled saline flush syringes are often utilized to ensure that a medicant dosage is fully deposited into a patient, used to separate multiple subsequent injections of medicants, or to clear a catheter of blood after a blood draw. A saline flush syringe is generally similar in type, quality, accuracy, and functionality as a syringe used for injection of medicants.

Sterile flush devices in the art generally come in two different varieties. A first type of current sterile flush device includes disposable syringes that generally include a barrel, a piston, a plunger, and a luer cap. A second type of sterile flush device includes a three piece assembly that includes a barrel, a plunger, and a luer cap. The plunger is designed to have a slight interference with the barrel so that a piston is not required. Both first and second types of sterile flush devices operate in a similar fashion and can come sterilized and prefilled with medicant. Additionally, each of the first and second types of sterile flush devices requires the manufacture of multiple components that must interact with one another to operate effectively, which increases the manufacturing costs of the devices.

The typical prefilled flush syringes often include extra capabilities that are not required if the syringe is only being used to flush a catheter. These additional capabilities often require additional components that increase the overall manufacturing costs, making the syringes more expensive. Further, because these additional capabilities are often not required, the additional expense incurred due to the additional components is unnecessary. Accordingly, what is desired is a less costly injection device that can be provided with only the necessary components, and thus with a reduced cost.

SUMMARY

The present invention relates to an alternative and less costly medicant injection device and more specifically to a medicant injection device including a compressible container such as a fluid bag or a bottle with bellows, which includes luer and luer lock features.

In one aspect an injection device includes a bellowed body configured to hold a liquid medicant and a luer fitting. The body includes a proximal end and a distal end, with a hollow tip at the proximal end. The luer fitting is configured to be positioned over the tip and sealed with the proximal end of the body. The bellowed body is compressible, such that a user can compress the body by forcing the distal end towards the proximal end, or vice versa, in order to eject fluid medicant contained in the body from the tip to inject same into a patient. In one aspect, the body can include an enlarged locking bellows and the distal end of the body can include an annular locking protrusion. The annular locking protrusion is configured to engage and lock with the enlarged locking bellows, while the enlarged locking bellows is configured to compress prior to compression of the remainder of the body. The engagement of the annular locking protrusion and the enlarged locking bellows functions to prime the injection device. In another aspect, the body includes a female locking tab located at the proximal end, and a chamber and male locking tab located at a distal end of the body and extending into the body. The male locking tab is configured to engage the female locking tab such that a user can engage the two during a final injection in order to prevent reflux, spring-back, or reuse of the injection device.

In another aspect an injection device includes a bellowed body configured to hold a liquid medicant and a luer fitting. The body includes a proximal end and a distal end, with a hollow tip and locking shoulder at the proximal end. The luer fitting is configured to be positioned over the tip and snap over the locking shoulder to secure the luer fitting to the body.

In another aspect an injection device includes a bag that is compressible. The bag could be secured within a resiliently flexible frame. The flexible frame includes a base, a luer/luer lock secured with the base, and two arms extending, and diverging, from the base. The bag is configured to hold a liquid medicant. The flexible frame and bag are compressible, such that a user can compress the flexible frame by forcing the first and second arms toward one another in order to eject fluid medicant contained in the bag from the luer/luer lock to inject same into a patient. In one aspect, the first arm can include a locking ridge, while the second arm can include a locking loop. The locking ridge and the locking loop are configured to engage one another such that a user can engage the two upon a completion of an injection in order to prevent reflux, spring-back, or reuse of the injection device.

A medicant injection device includes a compressible body, a tip, and an outer luer body. The compressible body includes a plurality of bellows, a proximal end, and a distal end, and defines an inner cavity for holding a liquid medicant. The tip is positioned at the proximal end of the compressible body. The outer luer body is positioned over and engaged with the tip to form a first fitting that is configured to be connected with a second fitting.

In another aspect a medicant injection device includes a compressible body, a receptacle connected to the compressible body, and a first fitting. The compressible body includes first and second arms each having a proximal end and a distal end, whereby the first and second arms are connected at their respective proximal end forming a proximal base. The receptacle defines an inner cavity for holding a liquid medicant. The first fitting is positioned at the proximal base and is configured to engage a second fitting. The compressible body is configured to be compressed by forcing the distal end of the first arm and the distal end of the second arm toward each other such that the fluid medicant contained in the inner cavity is ejected from the tip when the compressible body is compressed.

BRIEF DESCRIPTION OF THE DRAWINGS

The foregoing features of the disclosure will be apparent from the following Detailed Description, taken in connection with the accompanying drawings, in which:

FIG. 4b is a cross-sectional view of the injection device of FIG. 4a;

FIG. 9a is a perspective view of a partially manufactured injection device of FIG. 5;

FIG. 9b is a cross-sectional view of the injection device of FIG. 9a;

FIG. 9c is a perspective view of the injection device of FIG. 9a further manufactured;

DETAILED DESCRIPTION

Figure 1:
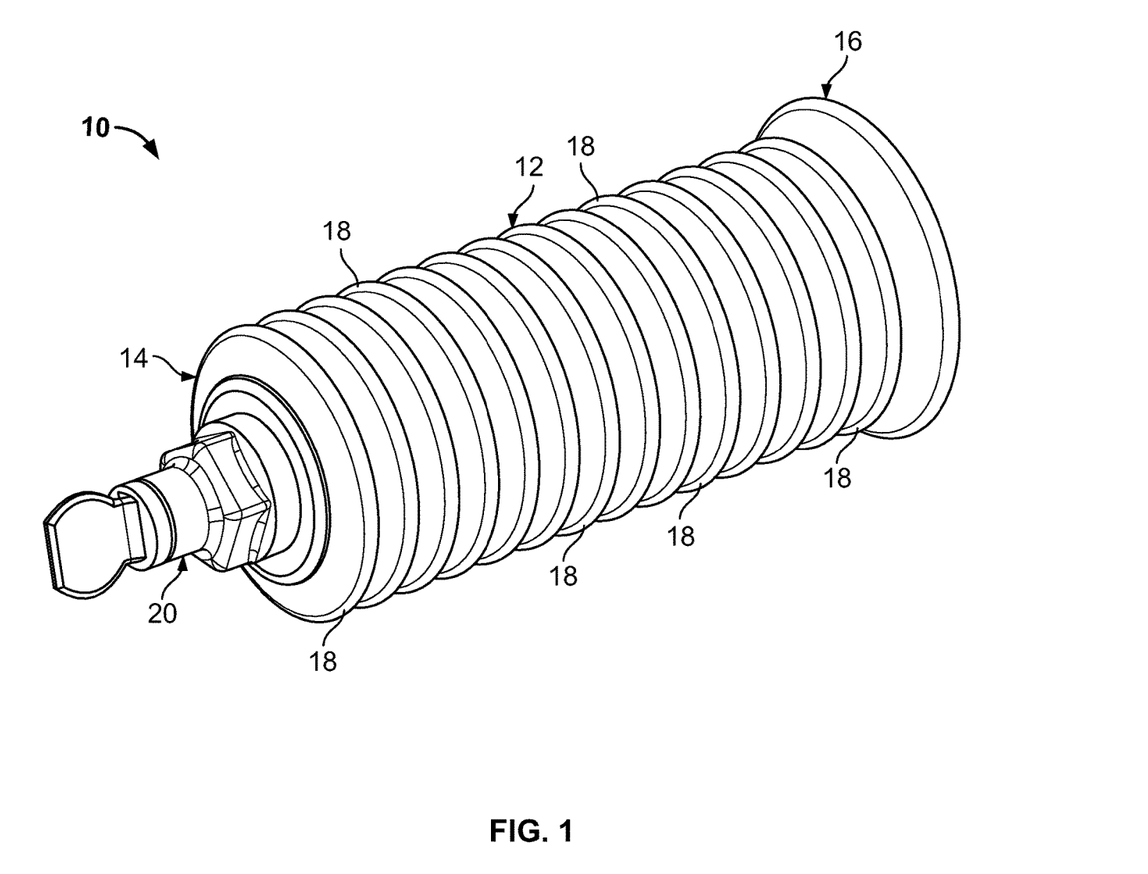
FIG. 1 is a front perspective view of a first embodiment of an injection device of the present disclosure.

FIGS. 1-4d show a medicant injection device of the present disclosure. FIG. 1 is a front perspective view of a compressible injection device 10 that is prefilled with a liquid medicant, e.g., saline, heparin, etc. The injection device 10 includes a bellowed body 12 having a proximal end 14, a distal end 16, and a plurality of bellows 18. The plurality of bellows 18 on the body 12 form a bellows structure such that the body 12 is compressible, e.g., the body 12 can be compressed so that the proximal end 14 and the distal end 16 are brought closer to one another. The injection device 10 also includes a luer fitting 20 formed by a tip 42 at the end of the bellows 18 and an outer luer body 56 positioned about the tip 42 and mounted to the injection device 10 at the proximal end 14. It is noted that one of ordinary skill in the art should understand that when reference is made to a "luer" or a "luer fitting" that this is not limited to only luer-type connections, but can be any dispensing geometry that is known or commonplace in the art.

Figure 2:
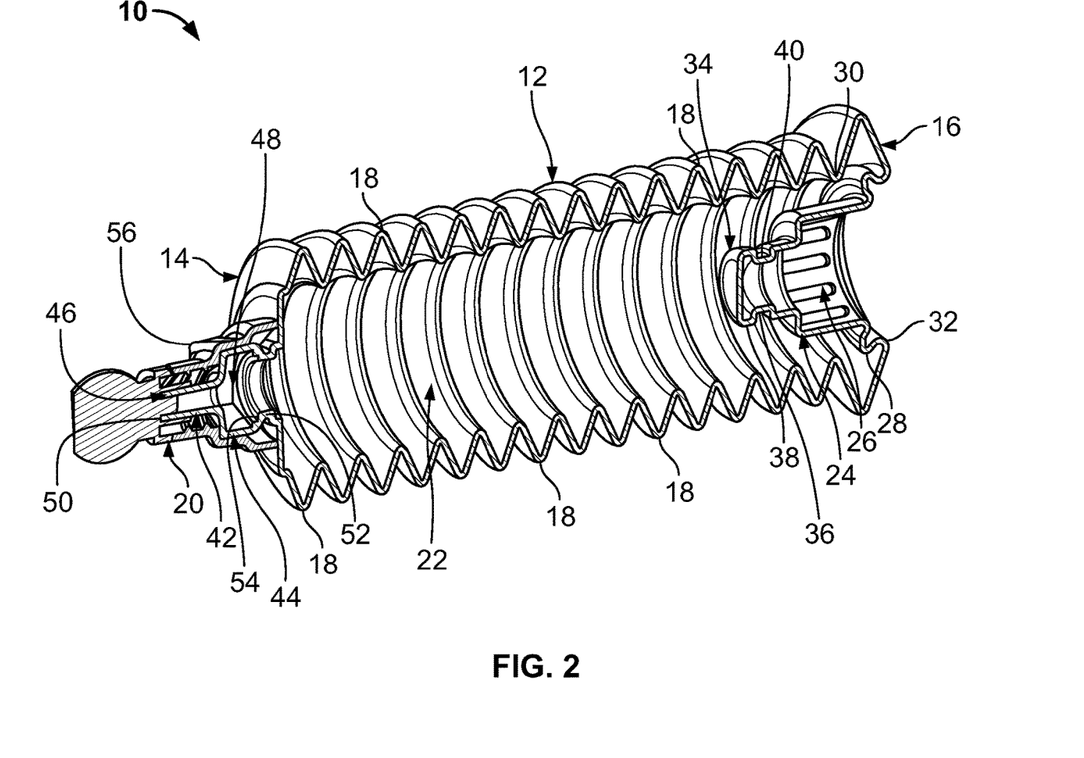
FIG. 2 is a sectional view of the injection device of FIG. 1.

FIG. 2 is a sectional view of the compressible injection device 10 showing the components thereof in further detail. As illustrated in FIG. 2, the body 12 defines an inner cavity 22 configured to be filled with and contain a liquid medicant. The distal end 16 of the body 12 includes a housing 24 that extends into the inner cavity 22. The housing 24 defines a chamber 26. The housing chamber 26 is connected to the distal end 16 by an annular locking protrusion 28 that extends radially outward to engage a locking bellows 30. The locking protrusion 28 and locking bellows 30 are discussed in greater detail below. The chamber 26 of the housing 24 is accessible by an aperture 32 located at a distal end of the housing 24 and formed in the distal end 16 of the body 12. The housing 24 can also include a male locking tab 34 extending from a proximal end of the housing 24. The male locking tab 34 includes a neck 36 that connects with a head 38. The neck 36 and head 38 are generally cylindrical components, with the head 38 having a greater diameter than the neck 36, thus forming a locking lip 40. The male locking tab 34 is configured to lockingly engage a portion of the proximal end 14 of the body 12, which is discussed in greater detail below. The housing 24 is separate from the inner cavity 22 such that fluid in the inner cavity 22 of the body 12 does not enter the housing 24. The chamber 26 of the housing 24 is configured to receive a secondary accessory such as a disinfectant product, such as a SwabCap disinfecting cap sold by Excelsior Medical Corp. The secondary accessory can be retained in the chamber 26 by a friction fit, snap-fit, threaded connection, adhesive, ultrasonic weld, or spin weld, for example.

The body 12 further includes a tip 42 extending from the proximal end 14 of the body 12. The tip 42 includes a female locking tab 44 extending from the proximal end 14 of the body 12 and a luer nozzle 46, e.g., a luer seal surface, extending from the female locking tab 44. The tip 42 is in communication with the inner cavity 22 of the body 12, such that the tip 42 defines an ejection chamber 48 and the nozzle 46 includes an aperture 50. The ejection chamber 48 and the aperture 50 allow fluid to pass from the inner cavity 22, through the ejection chamber 48, and out of the aperture 50. The female locking tab 44 can also include an annular neck 52 that defines an internal locking shoulder 54 and an external shoulder 55. The female locking tab 44 is configured to receive the male locking tab 34 such that the head 38 of the male locking tab 34 can be inserted into the ejection chamber 48. Once in the ejection chamber 48, the locking lip 40 of the male locking tab 34 engages the locking shoulder 54 of the female locking tab 44, preventing the bellows body 12 from being "uncompressed" or "spring-back." This is an anti-reflux feature that prohibits the injection device 10 from pulling fluids back out prior to removal, and prevents reuse of the device 10. Alternatively, the male locking tab 34 can engage the female locking tab 44 with a friction fit, and the male end 34 can include a tapered geometry.

Figure 3A:
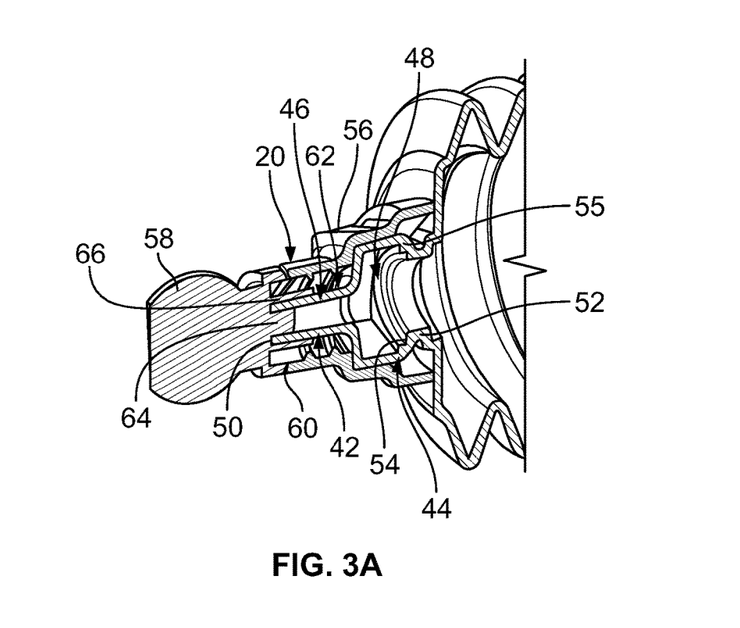
FIG. 3a is a partial sectional view of a luer fitting and tip of the injection device of FIG. 1.

FIG. 3a is a partial sectional view of the luer fitting 20 including the outer luer body 56 and the tip 42 of the injection device 10. A removable tab 58 is secured to the outer luer body 56 by a breakable interface 60. The outer luer body 56 is configured to surround the female locking tab 44 and be sealed to the distal end 14 of the body 12. The female locking tab 44 can include a specific geometry, e.g., an octagonal geometry, with the outer luer body 56 including a mating geometry such that when the outer luer body 56 mates with the female locking tab 44 rotation of the outer luer body 56 is prevented. The outer luer body 56 can include internal threading 62 for threadingly engaging a mating luer access device. It should be understood by one of ordinary skill in the art that the internal threading 62 is not a necessity, but instead the tip 42 can be inserted into a female luer using a luer slip configuration. The removable tab 58 includes first and second protrusions 64, 66. The first and second protrusions 64, 66 are configured to engage the luer nozzle 46 when the luer fitting 20 is positioned over the tip 42. Specifically, the first protrusion 64 is configured to be inserted into and plug the luer nozzle 46, while the second protrusion 66 is annular in nature and configured to be positioned about the luer nozzle 46. The luer fitting 20 is constructed such that a user can rotate the removable tab 58 to break the removable tab 58 off from the outer luer body 56 at the breakable interface 60, and then a user can compress the injection device 10 and expel any medicant contained therein.

In operation, a user first engages the removable tab 58 to break the removable tab 58 off from the luer fitting 20. The absence of the removable tab 58 provides a visual indicator that the device 10 has been opened, used, and/or that the sterile barrier has been breached. Accordingly, the removable tab 58 acts as a protective measure against undesired reuse of the device 10. The user then primes the device 10 by beginning to press the distal end 16 of the body 12 toward the proximate end 14. This initial compression causes the annular locking protrusion 28 to engage the first bellow, namely locking bellows 30, allowing for a prime action to take place ensuring that no air is inside the device 10. The locking bellows 30 can include a single ridge, or multiple ridges, and the locking protrusion 28 can be sized to engage more than one locking bellows 30. Further, one or more locking bellows 30 can be utilized to achieve the desired effect of a controlled dispense. Additionally, the locking bellows 30 can be sized larger or smaller, constructed of a thinner material, or constructed with other known geometries, so that it collapses easier or harder as desired. Alternatively, external geometry can be provided at the first bellows 18 adjacent the locking bellows 30 that allows a user to grasp thereon to assist with the priming injection and ensure that only the priming bellows 30 is collapsed. The locking bellows 30 provide a mechanical advantage where the locking bellows 30 predictably collapse, and will be urged to collapse first and lock with the annular locking protrusion 28 prior to any other bellows 18 collapsing. It is beneficial to have the locking bellows 30 collapse easier than the other bellows 18 so that the locking bellows 30 collapses without unnecessarily dispensing fluid from the device 10. Generally, the locking bellows 30 will have a lesser volume than the remainder of the bellows 18. After the locking bellows 30 are engaged with the annular locking protrusion 28, the device 10 is primed and stays primed until it is engaged to a luer access device. Once the device 10 is primed, a user connects the injection device 10 to a luer access device by engaging the luer fitting 20 with the luer access device, and the injection can begin. During the injection, the user then presses the distal end 16 of the body 12 toward the proximate end 14, compressing the body 12. The bellows 18 also allow a user to expand the body 12 during use in order to aspirate fluid and confirm patency of the injection line prior to injection. Additionally, during the injection, the user can withdraw fluid by allowing the bellows of the body 12 to "spring back" to an expanded state where a vacuum is created and fluid is pulled back into the device 10. This motion can be repeated as needed until a final compression is made. During the final compression, the user can compress the body 12 such that the bellows of the body 12 are fully compressed, and the male locking tab 34 is adjacent the female locking tab 44. The user then applies an increased force to force the male locking tab 34 into the female locking tab 44, creating a "final lock." The male locking tab 34 is retained in the female locking tab 44 through an engagement of the locking lip 40 of the male locking tab 34 engages the locking shoulder 54 of the female locking tab 44, preventing the bellows of the body 12 from being "uncompressed" or "spring-back." This is an anti-reflux feature that prohibits the injection device 10 from the unintentional withdraw of fluid. Furthermore, the bellowed body 12 provides the user with tactile feedback on how much force is required and how much pressure is generated during injection, as well as how much fluid has been injected.

The body 12 can also include exterior markings that provide a graduation marking function, allowing a user to determine an amount of medicant that has been ejected from the device 10. Additionally, the device 10 can include markings related to the volume of the device 10, the medicant contained in the device 10, etc.

Figure 3B:
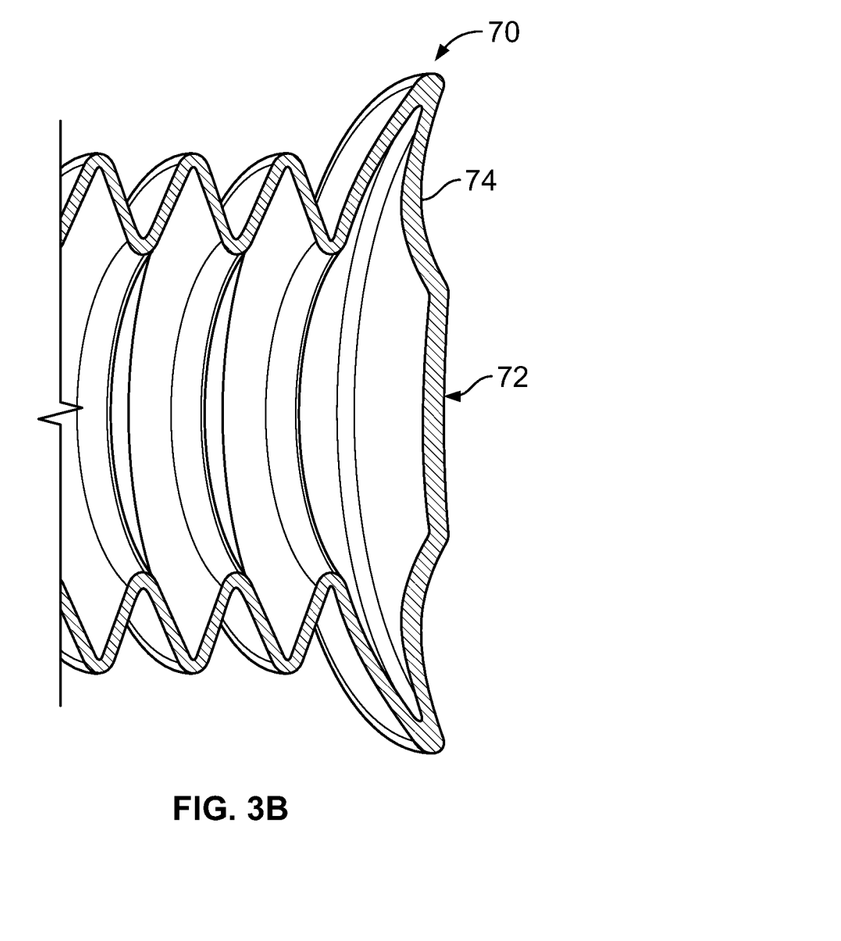
FIG. 3b is a partial sectional view showing a non-uniform walled locking bellow that inverts to generate a priming function.

FIG. 3b is a partial sectional view showing a non-uniform walled locking bellow 70 that inverts to generate a priming function, and which can be used in place of the locking below 30 of the injection device 10. The locking bellow 70 includes a non-uniform wall 72 that is capable of deflecting and inverting in on itself, creating a slight concavity 74. Specifically, as pressure is applied to the non-uniform wall 72 it deflects until it reaches an inflection point where the wall 72 inverts itself inward, e.g., toward the proximal end 14 of the device 10, and locks in this position, e.g., nested in on itself. This provides a priming function wherein ensuring that no air is inside the device 10. Further, the locking bellow 70 remains inverted, and locked, in the primed position.

It should be understood by one of ordinary skill in the art that the male locking tab 34 and the female locking tab 44 are optional components, and the injection device 10 can be constructed without these components as a non-locking device.

It should also be understood by one of ordinary skill in the art that the housing 24 is not required and the injection device 10 can be provided without the housing 24.

It should also be understood by one of ordinary skill in the art that the annular locking protrusion 28 and the locking bellows 30 are also option components, and the injection device 10 can be constructed without these components.

It should also be understood by one of ordinary skill in the art that the outer luer body 56 can be connected to the tip 42 by means other than a snap-fit connection, for example, friction fit, threaded connection, adhesive, ultrasonic weld, or spin weld, etc.

Figure 4A:
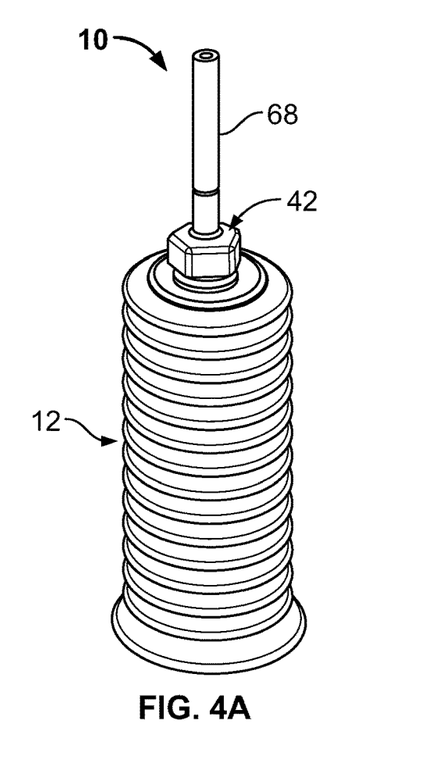
FIG. 4a is a perspective view of a partially manufactured injection device of FIG. 1.
Figure 4B:
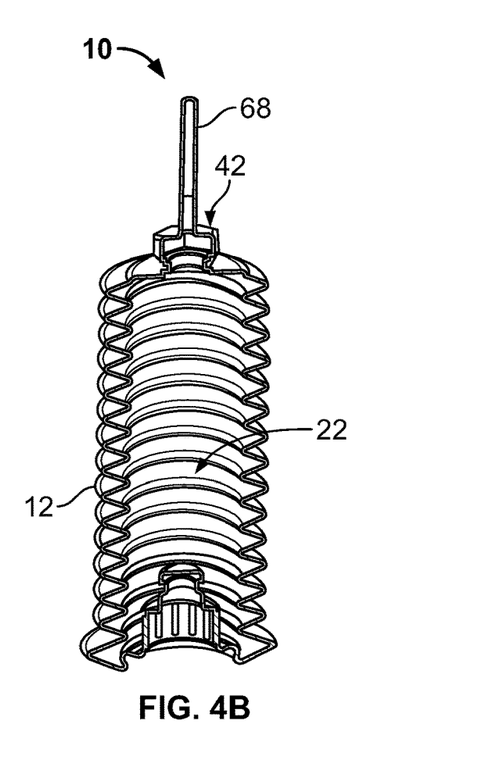
Figure 4C:
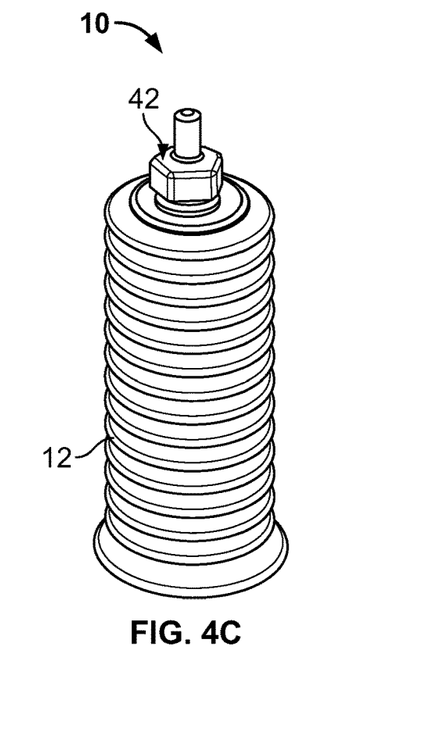
FIG. 4c is a perspective view of a third step of manufacturing the injection device of FIG. 4a further manufactured.
Figure 4D:
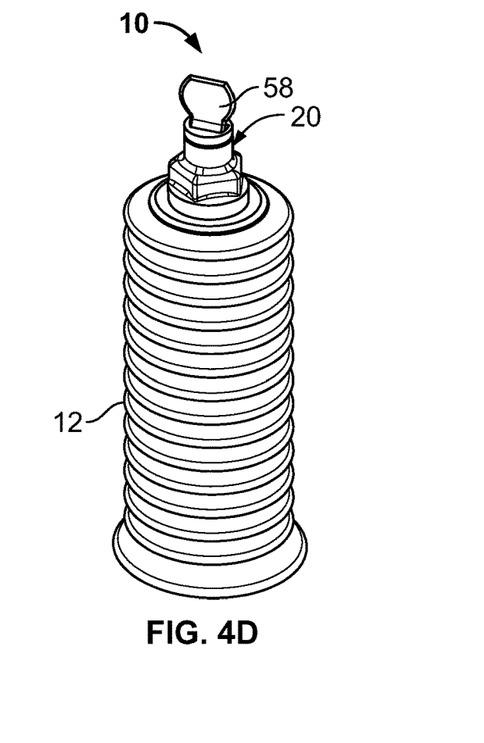
FIG. 4d is a perspective view of the injection device of FIG. 4a further manufactured.

FIGS. 4a-4d illustrate the injection device 10 at stages during manufacturing. FIG. 4a illustrates the bellowed body 12 of the injection device 10 first formed with a fill tip 68. The body 12 can be formed through blow molding, or other processes that are known in the art. FIG. 4b is a cross-section of FIG. 4a, showing where the injection device 10 is filled through the fill tip 68 and the tip 42, such that the inner cavity 22 is filled with a liquid medicant. FIG. 4c illustrates another partially manufactured device where the fill tip 68 is trimmed from the tip 42. FIG. 4d illustrates another partially manufactured device where the outer luer body 56, including luer threads, and the removable tab 58, are pressed and trapped in place on the tip 42 to seal the tip 42. The luer fitting 20 can be injection molded. This allows the outer luer body 56 to remain sterile during manufacture, and allows the outer luer body 56 and removable tab 58 to be manufactured as a single part. During the manufacturing process, a sterile barrier is provided for both the luer threads and the fluid path that leads to the inner cavity 22 by the application of the outer luer body 56, which creates a tortuous path at the attachment of the outer luer body 56 to the tip 42.

Figure 5:
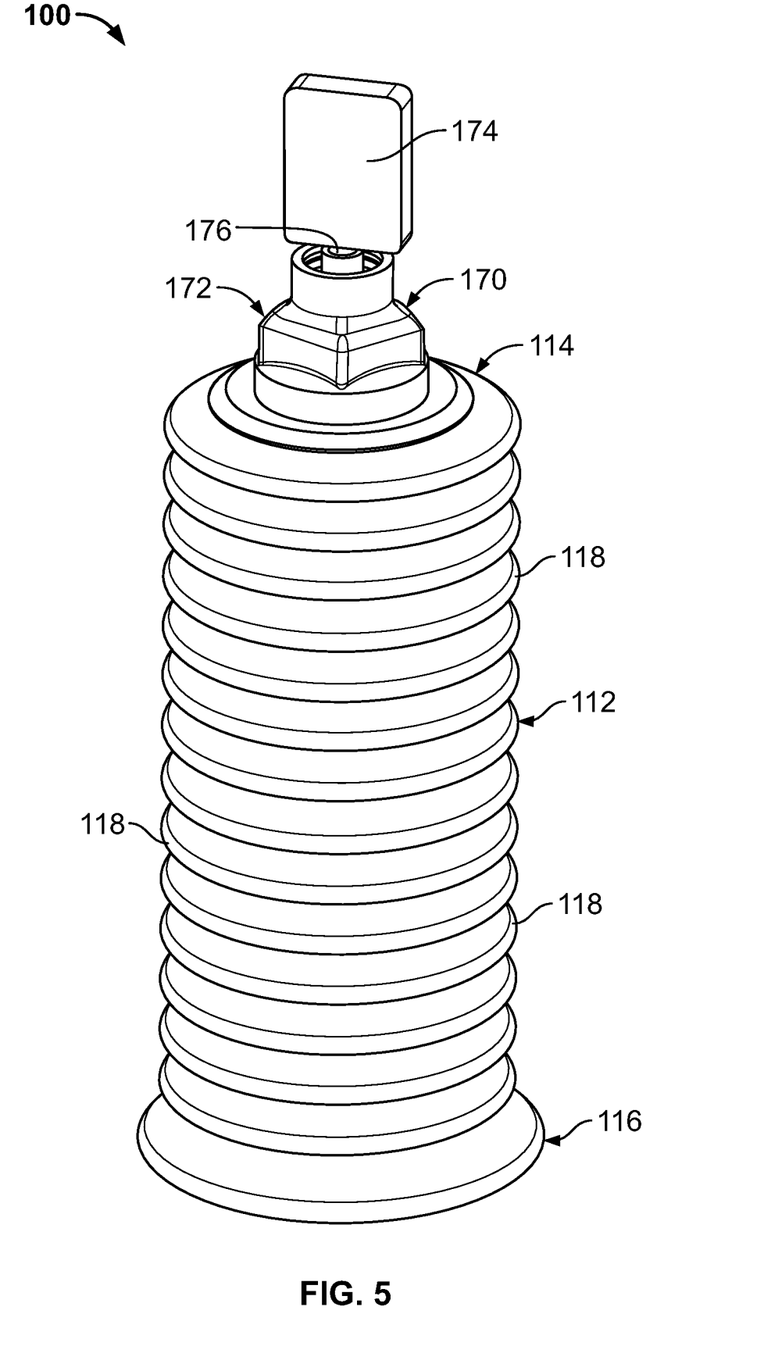
FIG. 5 is a front perspective view of another injection device of the present disclosure.
Figure 6:
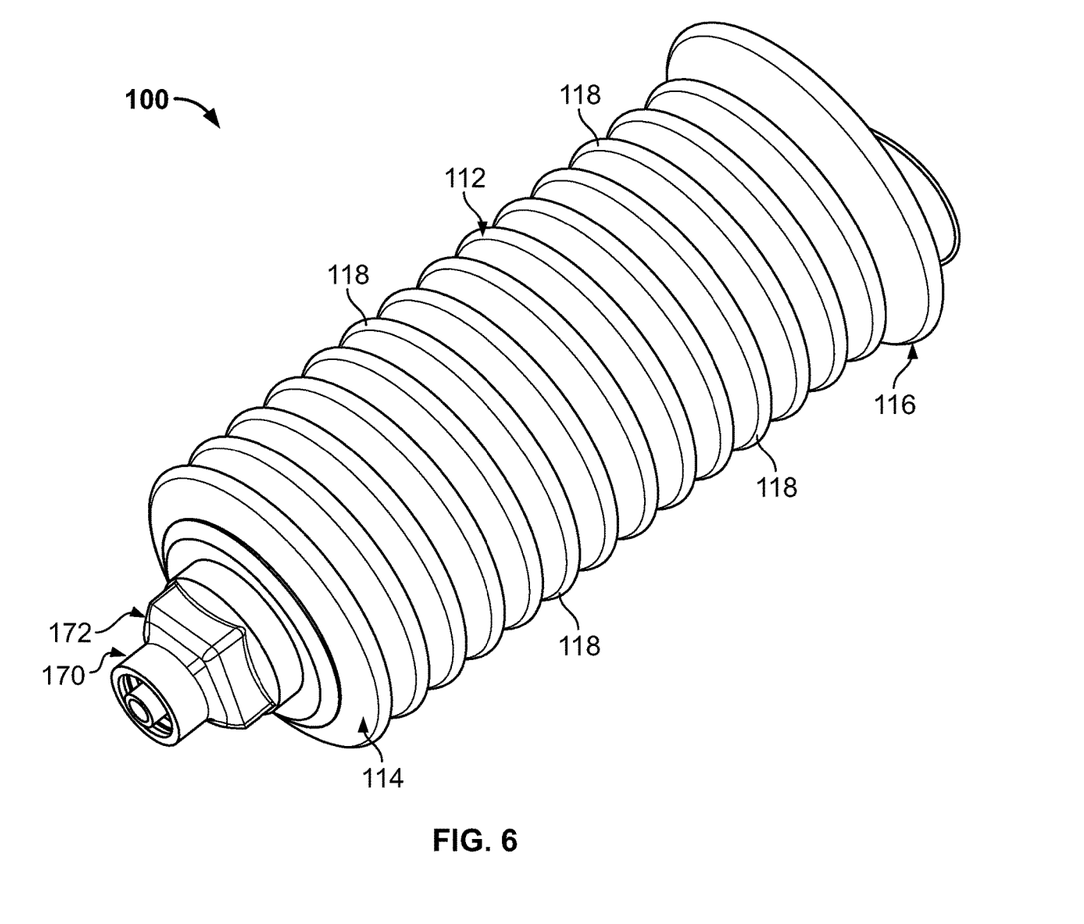
FIG. 6 is a front perspective view of the injection device of FIG. 5 with a removable tab removed.

FIGS. 5-9c illustrate another injection device 100 incorporating an alternative luer fitting for the injection device 10 of FIGS. 1-4d. Elements illustrated in FIGS. 5-9c that correspond substantially to the elements described above with reference to FIGS. 1-4d have been designated with corresponding reference numerals. The injection device 100 shown in FIGS. 5-9c operates and is constructed consistent with the foregoing description of the injection device 10 of FIGS. 1-4d, unless stated otherwise. Particularly, FIG. 5 is a perspective view of the injection device 100 that includes a bellowed body 112 having a plurality of bellows 118 and defining an inner cavity 122. The body 112 has a proximal end 114 and a distal end 116. The injection device 100 includes an alternative luer fitting 170 having an alternative outer luer body 172 secured to the tip 142. The luer fitting 170 can include the outer luer body 172, and a removable tab 174 is secured to the outer luer body 172 by a breakable interface 176. The luer fitting 170 is constructed such that a user can rotate the removable tab 174 to break the removable tab 174 off from the outer luer body 172 at the breakable interface 176, thus allowing a user to compress the injection device 100 and expel any medicant contained therein. FIG. 6 is a front perspective view of the injection device 100 with the removable tab 174 removed from the outer luer body 172.

Figure 7:
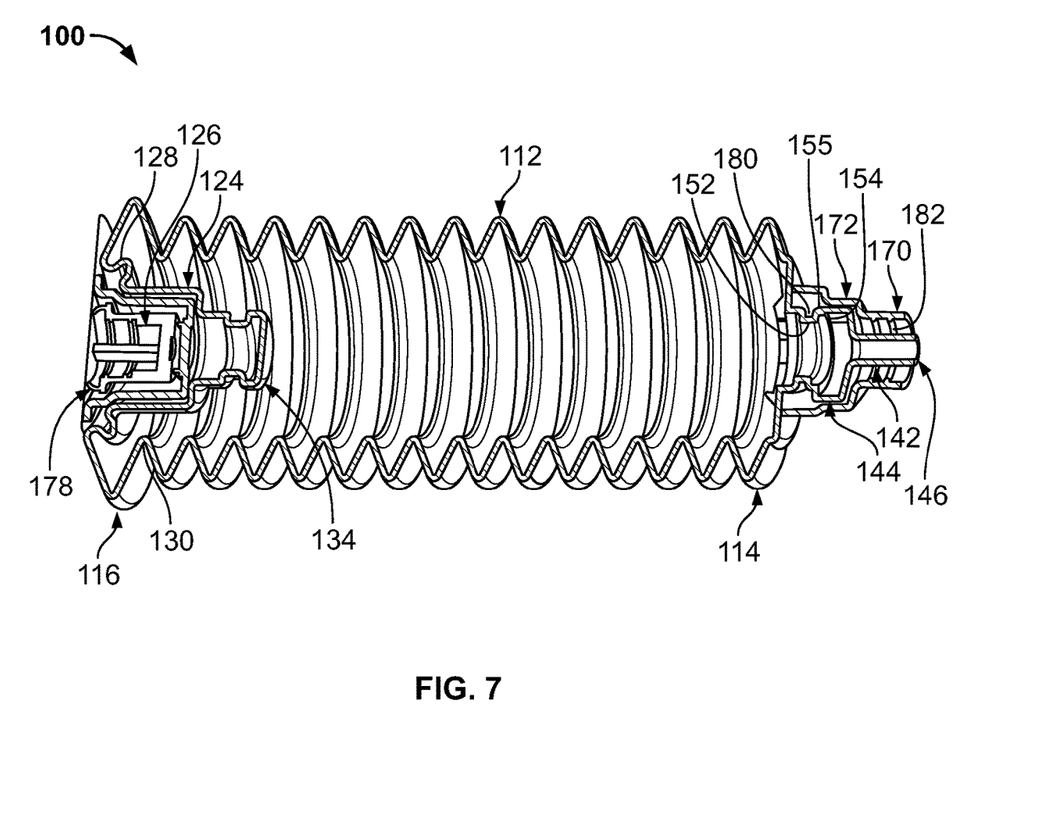
FIG. 7 is a sectional view of the injection device of FIG. 6.
Figure 8:
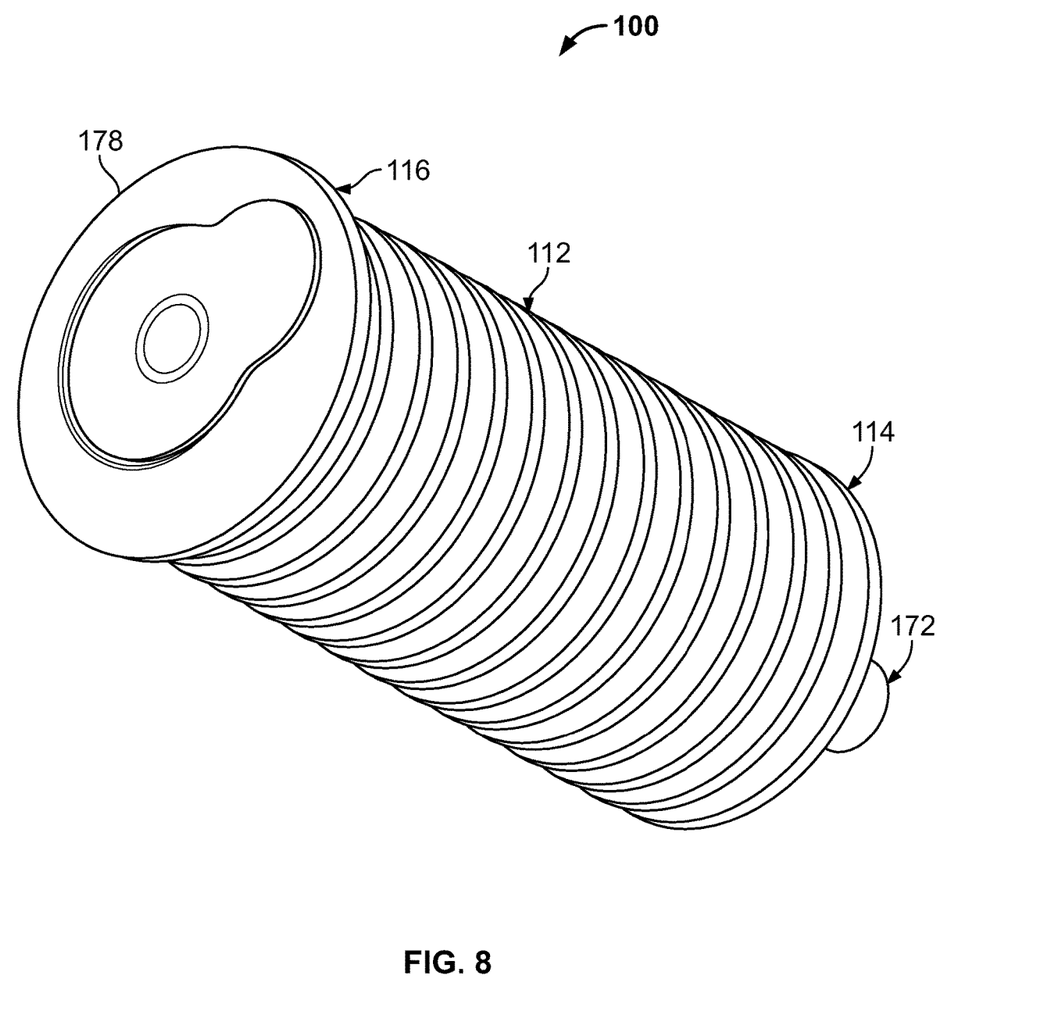
FIG. 8 is a rear perspective view of the injection device of FIG. 6.

FIG. 7 is a sectional view of the injection device 100 showing the luer fitting 170 in greater detail. Similar to the injection device 10 of FIGS. 1-4d, the distal end 116 of the body 112 includes a housing 124 that extends into the inner cavity 122, and includes a male locking tab 134. The housing 124 defines a chamber 126 that is configured to receive a secondary device 178 such as a cleaning device, such as a SwabCap disinfecting cap sold by Excelsior Medical Corp (see also FIG. 8 which is a rear perspective view of the injection device 100 having a cleaning device 178 within the chamber 126). The secondary accessory 178 can be retained in the chamber 26 by a friction fit, snap-fit, threaded connection, adhesive, ultrasonic weld, or spin weld, for example. The proximal end 114 includes a tip 142 extending therefrom that can include a female locking tab 144 and a nozzle 146. The female locking tab 144 includes an annular neck 152 that defines an internal locking shoulder 154 and an external shoulder 155. The outer luer body 172 of the luer fitting 170 includes an internal annular ridge 180 that is configured to engage the external shoulder 155 of the female locking tab 144. Specifically, the outer luer body 172 is configured to be positioned over the tip 142, and pressed toward the distal end 116 of the injection device 100 until the internal annular ridge 180 snaps over the female locking tab 144 and engages the external shoulder 155. It should also be understood by one of ordinary skill in the art that the outer luer body 172 can be connected to the tip 142 by means other than a snap-fit connection, for example, friction fit, threaded connection, adhesive, ultrasonic weld, or spin weld, etc. Accordingly, the annular neck 152 defines a notch that the internal annular ridge 180 of the outer luer body 172 engages. The outer luer body 172 can include internal threading 182 for threadingly engaging a mating luer access device.

The injection device 100 of FIGS. 5-9c operates in substantial conformity with the injection device 10 of FIGS. 1-4d described in detail above.

It should be understood by one of ordinary skill in the art that the male locking tab 134 and the female locking tab 144 are optional components, and the injection device 100 can be constructed without these components as a non-locking device.

It should also be understood by one of ordinary skill in the art that the housing 124 is not required and the injection device 100 can be provided without the housing 124.

It should also be understood by one of ordinary skill in the art that the annular locking protrusion 128 and the locking bellows 130 are also optional components, and the injection device 100 can be constructed without these components.

Figures 9A, 9B, 9C:
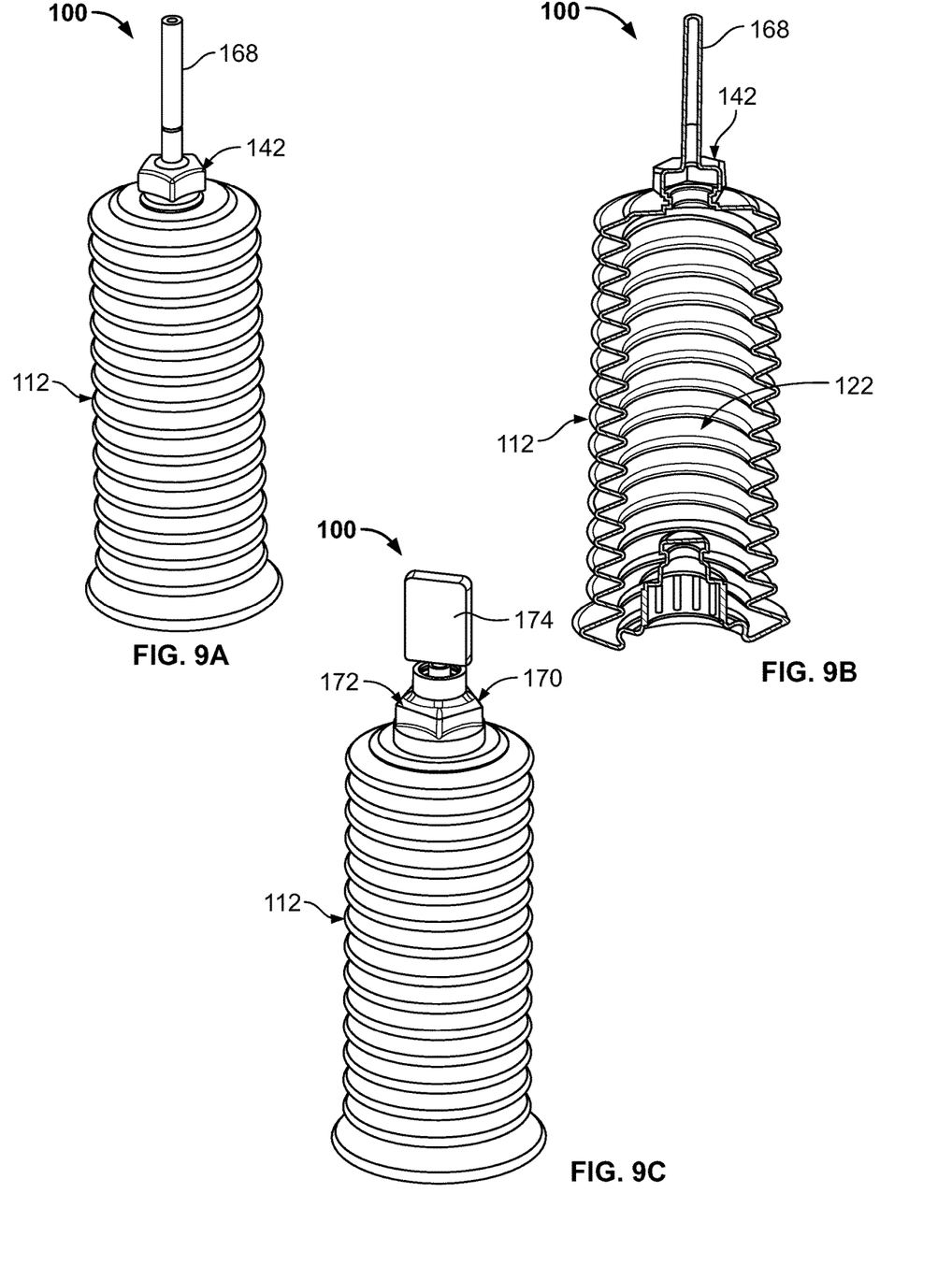

FIGS. 9a-9c illustrate the injection device 100 at stages during manufacturing. FIG. 9a illustrates a bellowed body 112 of the injection device 100 first formed with a fill tip 168. The body 112 can be formed through blow molding, injection molding, or other processes that are known in the art. FIG. 9b illustrates a second manufacturing step where the injection device 100 is filled through the fill tip 168 and the tip 142, such that the inner cavity 122 is filled with a liquid medicant. FIG. 9c illustrates that the outer luer body 172 is snapped onto the tip 142. The fill tip 162 is then compressed and heat sealed, and optionally trimmed, to form the removable tab 174, thus sealing the inner cavity 122. The outer luer body 172, the tip 142, the fill tip 168, and the removable tab 174 can be injection molded. Accordingly, compressing the fill tip 168 to form the removable tab 174 allows for the known manufacturing processes to be leveraged. During the manufacturing process the fluid path that leads to the inner cavity 122 remains sterile. The threaded area of the outer luer body 172, the interior of the outer luer body 172, and the tip 142 can be kept sterile through additional packaging.

Figure 10:
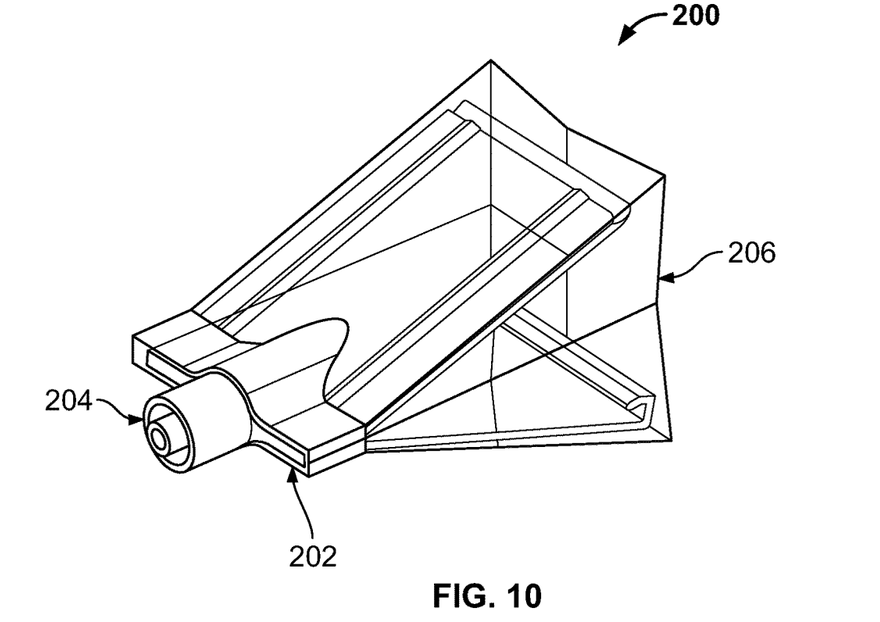
FIG. 10 is a perspective view of another aspect of an injection device of the present disclosure.
Figure 11:
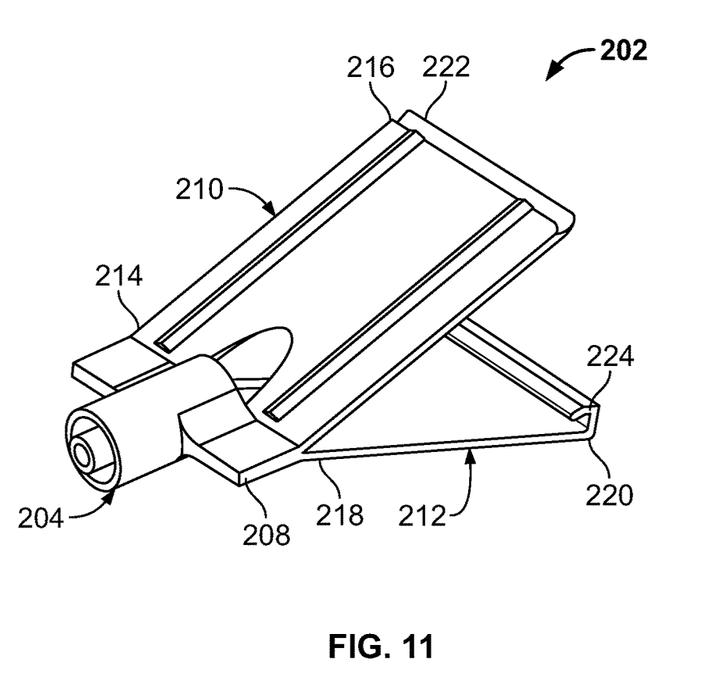
FIG. 11 is a perspective view of a frame of the injection device of FIG. 10.

FIGS. 10 and 11 illustrate another aspect of the medicant injection device of the present disclosure. FIG. 10 is a perspective view of an injection device 200. The injection device 200 includes a collapsible frame 202, a luer/luer-lock fitting 204, and a receptacle 206, such as a container or bag. The receptacle 206 can be a laminate film foil bag constructed of, for example, polyethylene terephthalate (PET), polyethylene (PE), foil, linear low density polyethylene (LLDPE), which are common for fluid storage or other suitable structures. The receptacle 206 can also be made of a malleable material such as thick foil that does not "springback" and remains in a collapsed state after compression. The receptacle 206 can be heat sealed to the frame 202 or attached by other appropriate means, e.g., adhesive, ultrasonic welding, spin welding, over molding, etc. The receptacle 206 is configured to contain a liquid medicant. The luer/luer-lock fitting 204 can be molded as a single piece with the collapsible frame 202, or can be molded as a separate piece and attached to the collapsible frame 202. Alternatively, the receptacle 206 can be attached to the fitting 204 directly and the collapsible frame 202 not utilized.

FIG. 11 is a perspective view of the collapsible frame 202 that can provide support for the receptacle 206. The collapsible frame 202 includes a proximal base 208, and first and second arms 210, 212 extending distally from the proximal base 208. The first and second arms 210, 212 can be configured as plate members. The first arm 210 includes a proximal end 214 and a distal end 216, the proximal end 214 being attached to the proximal base 208. The second arm 212 includes a proximal end 218 and a distal end 220, the proximal end 218 being attached to the proximal base 208. Thus, the first and second arms 210, 212 are configured wherein their respective proximal end, 214, 218 are attached with the proximal base 208, and their distal ends 216, 220 diverge. The distal ends 216, 220 of the first and second arms 210, 212 can be moved together by squeezing them together to pivot the arms about the proximal base 208 to cause the liquid medicant contained in the receptacle 206 to be forced out of the luer/luer-lock fitting 204 and injected into a patient. Additionally, the distal ends 216, 220 of the first and second arms 210, 212 can be pulled apart, providing an aspiration function so that the connected line can be checked for patency prior to injection. The collapsible frame 202 could be spring-loaded to allow a user to repeatedly inject and withdrawal as needed. Further, a ratcheting mechanism can be included between the first and second arms 210, 212 to provide a priming function and allow a metered or controlled injection. The frame 202 could be adhered to the receptacle 206 by, for example, bonding or glue, to provide structural support and increased fluid control. Additionally, the first arm 210 can include a locking ridge 222 at the distal end 216, while the second arm 212 can include a locking loop 224 at the distal end 220. The locking ridge 222 and the locking loop 224 are configured to have mating geometries such that the locking loop 224 can engage and lock with the locking ridge 222 when the medicant is fully injected to prevent the first and second arms 210, 212 from being "uncompressed" or "springing-back." This is an anti-reflux feature that prohibits the injection device 200 from the unintentional withdraw of fluid, as well as preventing reuse of the injection device. The luer/luer-lock fitting 204 can include a check valve incorporated therein to prevent fluid from flowing back into the injection device 200, e.g., reflux, and allows fluid to only flow out of the injection device 200. The injection device can also include a luer cap to seal the luer/luer-lock fitting 204 and retain the sterility of the luer/luer-lock fitting 204. The collapsible frame 202 can be injection molded. It should be understood by one of ordinary skill in the art that the collapsible frame 202 can be provided on the inside or the outside of the receptacle 206.

In operation, a user connects the injection device 200 to a luer access device by engaging the luer/luer-lock fitting 204 with the luer access device, such as threaded engagement, and the injection can proceed. During the injection, the user presses the distal end 216 of the first arm 210 and the distal end 220 of the second arm 212 toward each other, compressing the receptacle 206. Additionally, during the injection, the user can withdraw fluid by allowing the first and second arms 210, 212 to "spring back" to an expanded state where a vacuum is created and fluid is pulled back into the device 200. This motion can be repeated as needed until a final compression is made. During the final compression, the user compresses the first and second arms 210, 212 such that the receptacle 206 is fully compressed, and the locking ridge 222 is adjacent the locking loop 224. The user then applies an increased force to force the locking ridge 222 into the locking loop 224, creating a "final lock." The locking ridge 222 is retained in the locking loop 224 through an engagement of the two, preventing the compressible frame 202 from being "uncompressed" or "spring-back." This is an anti-reflux feature that prohibits the injection device 200 from the unintentional withdraw of fluid. Furthermore, the construction of the injection device 200 provides the user with tactile feedback on how much force is required and how much pressure is generated during injection, as well as how much fluid has been injected.

The injection devices described herein can be steam sterilized or may make use of various high volume sterilization methods such as gamma sterilization or ethylene oxide (EtO) sterilization. Additionally, the injection devices described herein can be sized to accommodate common sized syringe volumes, e.g., 3 milliliters, 5 milliliters, 10 milliliters, etc. Further, the injection devices described herein are sized to create a mechanical leverage. A target nominal value of seven pounds per square inch to deliver the injection can be targeted, with a high value of twenty-four pounds per square inch. The injection devices are generally constructed to include a mechanical advantage requiring the lowest pressure necessary. The injection devices are constructed without non-essential functionality to reduce cost. Still further, the injection devices described herein are sterile and disposable, provides a barrier to maintain sterility, and conform to all International Organization for Standardization (ISO) luer lock standards such as ISO 594.

It should be understood by one of ordinary skill in the art that the locking ridge 222 and the locking loop 224 are optional components, and the injection device 200 can be constructed without these components such that it is a non-locking device.

Additionally, each of the devices 10, 100, 200 can include a check valve and/or a two-way pressure activated valve that only allows fluid flow when a certain pressure is achieved.

It is to be understood that the foregoing description is not intended to limit the spirit or scope of the disclosure. It will be understood that the aspects of the disclosure described herein are merely exemplary and that a person skilled in the art may make many variations and modification without departing from the spirit and scope of the disclosure. All such variations and modifications, including those discussed above, are intended to be included within the scope of the disclosure.

What is claimed is:
1. A medicant injection device, comprising:
   a compressible body including a first arm having a proximal end and a distal end,
   and a second arm having a proximal end and a distal end, wherein a portion of the first arm and a portion of the second arm are connected at their respective proximal ends forming a proximal base;
   a receptacle interconnected with the compressible body and defining an inner cavity for holding a liquid medicant; and
   a first fitting integrally formed with the proximal base and positioned at the proximal base and configured to engage a second fitting,
   wherein the compressible body is configured to be compressed by forcing the distal end of the first arm and the distal end of the second arm toward each other such that the liquid medicant contained in the receptacle is ejected from the first fitting when the compressible body is compressed.
2. The medicant injection device of claim 1, wherein the receptacle comprises a bag, and
   wherein the first fitting is a first luer fitting.
3. The medicant injection device of claim 2, wherein the receptacle comprises one of polyethylene terephthalate, polyethylene, foil, or linear low density polyethylene.
4. The medicant injection device of claim 1, wherein the first arm includes a locking ridge and the second arm includes a locking loop, the locking ridge and the locking loop configured to engage each other and lock the compressible body in a compressed position.
5. The medicant injection device of claim 1, further comprising a removable tab engaged to a tip and configured to prevent liquid medicant from being expelled from the tip.
6. The medicant injection device of claim 5, further comprising a breakable interface configured to secure the removable tab to the tip.

7. The medicant injection device of claim 1, further comprising a ratchet mechanism provided between the first arm and the second arm to enable air priming.

8. The medicant injection device of claim 1, wherein the compressible body is prefilled with the liquid medicant.

9. The medical injection device of claim 1, wherein the proximal end of the first arm has a cutout region which does not connect to the proximal end of the second arm, the cutout region extending through a planar portion of the first arm.

10. The medical injection device of claim 1, wherein the first and second arms are plates each having an inner face and an outer face, and wherein at least a portion of the inner face is configured to engage the receptacle when the compressible body is compressed.

11. The medicant injection device of claim 1, wherein the first arm includes at least one longitudinal rib extending along an exterior surface of the first arm.

12. A medicant injection device, comprising:
a compressible body including a first arm and a second arm, the first arm having a proximal end and a distal end, the second arm having a proximal and a distal end, wherein a first portion of the proximal end of the first arm is connected to a first portion of the proximal end of the second arm forming a first region of a proximal base, and a second portion of the proximal end of the first arm is connected to a second portion of the proximal end of the second arm forming a second region of the proximal base;
a receptacle interconnected with the compressible body and defining an inner cavity for holding a liquid medicant; and
a first fitting positioned between the first and second regions of the proximal base,
wherein at least one of the first arm and the second arm is at least partially disposed within the receptacle, and wherein the compressible body is configured to be compressed by forcing the distal end of the first arm and the distal end of the second arm toward each other such that the liquid medicant contained in the receptacle is ejected from the first fitting when the compressible body is compressed.

13. The medicant injection device of claim 12, wherein the receptacle comprises a bag, and
wherein the first fitting is a first luer fitting.

14. The medicant injection device of claim 12, wherein the first arm includes a locking ridge and the second arm includes a locking loop, the locking ridge and the locking loop configured to engage each other and lock the compressible body in a compressed position.

15. The medicant injection device of claim 12, further comprising a removable tab engaged to a tip and configured to prevent liquid medicant from being expelled from the tip.

16. The medicant injection device of claim 12, wherein the compressible body is prefilled with the liquid medicant.

17. The medical injection device of claim 12, wherein the first and second arms extend distally from the proximal base, the first and second arms diverging from one another.

18. The medicant injection device of claim 12, wherein the first arm and the second arm are entirely disposed within the receptacle.

19. The medicant injection device of claim 12, wherein the receptacle is secured to an exterior surface of the proximal base.

20. The medicant injection device of claim 12, wherein the receptacle is secured to an exterior surface of the first fitting.

21. The medicant injection device of claim 12, wherein the first portion of the proximal end of the first arm is directly connected to the first portion of the proximal end of the second arm, and the second portion of the proximal end of the first arm is directly connected to the second portion of the proximal end of the second arm.

22. The medicant injection device of claim 12, wherein the first fitting is integrally formed with at least one of the first arm and the second arm.

* * * * *

UNITED STATES PATENT AND TRADEMARK OFFICE
CERTIFICATE OF CORRECTION

PATENT NO. : 10,737,031 B2
APPLICATION NO. : 15/653899
DATED : August 11, 2020
INVENTOR(S) : Christopher E. Gardner et al.

It is certified that error appears in the above-identified patent and that said Letters Patent is hereby corrected as shown below:

In the Claims

In Claim 9 (Column 11, Line 6 (approx.)), "medical injection device" is replaced with "medicant injection device";

In Claim 10 (Column 11, Line 10 (approx.)), "medical injection device" is replaced with "medicant injection device";

In Claim 17 (Column 12, Line 17 (approx.)), "medical injection device" is replaced with "medicant injection device".

Signed and Sealed this
Fifteenth Day of September, 2020

Andrei Iancu
*Director of the United States Patent and Trademark Office*